United States Patent
Sweeney et al.

(10) Patent No.: US 6,526,313 B2
(45) Date of Patent: Feb. 25, 2003

(54) SYSTEM AND METHOD FOR CLASSIFYING CARDIAC DEPOLARIZATION COMPLEXES WITH MULTI-DIMENSIONAL CORRELATION

(75) Inventors: Robert J. Sweeney, Woodbury, MN (US); William Hsu, Ann Arbor, MI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 51 days.

(21) Appl. No.: 09/874,892

(22) Filed: Jun. 5, 2001

(65) Prior Publication Data

US 2002/0183639 A1 Dec. 5, 2002

(51) Int. Cl.$^7$ ............................................. A61B 5/0402
(52) U.S. Cl. ........................................ 600/515; 600/512
(58) Field of Search ................................ 600/515, 512, 600/516, 517; 128/920, 923; 607/9

(56) References Cited

U.S. PATENT DOCUMENTS 4,802,491 A * 2/1989 Cohen et al. ............... 600/515
4,947,857 A * 8/1990 Albert et al. ............... 600/509

* cited by examiner

Primary Examiner—Kennedy Schaetzle
(74) Attorney, Agent, or Firm—Schwegman, Lundberg, Woessner & Kluth, P.A.

(57) ABSTRACT

A system and method for classifying cardiac depolarization complexes in which waveforms of a depolarization complex are sensed by separate electrodes and correlated with template waveforms of a template depolarization complex. The system is particularly suitable for incorporation into a cardiac rhythm management device such as an implantable cardioverter/defibrillator or pacemaker in order to facilitate arrhythmia prediction and/or prevention.

20 Claims, 3 Drawing Sheets

SYSTEM AND METHOD FOR CLASSIFYING CARDIAC DEPOLARIZATION COMPLEXES WITH MULTI-DIMENSIONAL CORRELATION

FIELD OF THE INVENTION

This invention pertains to systems and methods for cardiac rhythm management and, in particular, for processing sensed depolarization waveforms produced by the electrical activity of the heart.

BACKGROUND

The human heart normally maintains its own well-ordered intrinsic rhythm through the generation of stimuli by pacemaker tissue that results in a wave of depolarization that spreads through specialized conducting tissue and then into and throughout the myocardium. The well-ordered propagation of electrical depolarizations through the heart causes coordinated contractions of the myocardium that results in the efficient pumping of blood. In a normally functioning heart, stimuli are generated under the influence of various physiological regulatory mechanisms to cause the heart to beat at a rate that maintains cardiac output at a level sufficient to meet the metabolic needs of the body. Abnormalities of excitable cardiac tissue, however, can lead to abnormalities of heart rhythm by affecting either impulse generation or propagation. Since such arrhythmias can be hemodynamically compromising and predispose to thromboembolic events, therapeutic intervention is usually warranted.

One therapeutic modality for treating certain types of arrhythmias is an implantable cardiac rhythm management device that delivers therapy to the heart in the form of electrical stimuli. Such implantable devices include cardiac pacemakers that deliver timed sequences of low energy pacing pulses to the heart via one or more electrodes disposed in or about the heart in response to sensed cardiac events and lapsed time intervals. Pacemakers are often used to treat patients with bradycardia and atrioventricular conduction defects. Cardiac rhythm management systems also include cardioverter/defibrillators (ICD's) that are capable of delivering higher energy electrical stimuli to the heart and are often used to treat patients prone to fibrillation and other tachyarrhythmias. A defibrillator delivers a high energy electrical stimulus or shock to the heart to depolarize all of the myocardium and render it refractory in order to terminate the arrhythmia, allowing the heart to reestablish a normal rhythm for the efficient pumping of blood. ICD's are often combined with a pacemaker capable of pacing the heart in such a manner that the heart rate is slowed, a pacing mode referred to as anti-tachyarrhythmia pacing (ATP). ATP therapy includes a number of different protocols for delivering pulses to the heart which tend to disrupt reentrant circuits responsible for the arrhythmia. In addition to ICD's and pacemakers, cardiac rhythm management devices also include drug delivery devices, and any other implantable or external devices for diagnosing, monitoring, or treating cardiac arrhythmias.

Since cardiac rhythm management devices are often configured to be capable of delivering a number of different electrotherapies to the heart, it is useful for the device to be programmed to recognize particular arrhythmias. That is, if an arrhythmia can be classified as a type known to be amenable to a certain therapeutic mode capable of being delivered by the device, the arrhythmia can be treated more effectively. One way of characterizing an arrhythmia is by the abnormal depolarization complex that results as the wave of excitation spreads through the myocardium during a single heartbeat. Furthermore, some depolarization complexes may represent arrhythmogenic conditions that predispose to the development of an arrhythmia. If such a condition can be recognized, preventive therapy can be delivered before the arrhythmia occurs. It is toward the objective of classifying such depolarization complexes that the present invention is primarily directed.

SUMMARY OF THE INVENTION

In accordance with the invention, a cardiac depolarization complex is sensed by a plurality of separate electrodes that sense depolarization waveforms occurring at different areas of the heart. The sensed waveforms are then compared to the corresponding depolarization waveforms of a template depolarization complex, where the template depolarization complex may be representative of an arrhythmogenic condition. If the sensed and template waveforms are judged to be similar enough, the sensed depolarization complex can be classified as being equivalent to the template depolarization complex. In order to assess the similarity of the template and depolarization complexes, the waveforms corresponding to each of the plurality of sensing electrodes can be treated as different components of a multi-dimensional vector. A multi-dimensional correlation operation is performed between the vector for the sensed depolarization complex and the vector for the template depolarization complex. The similarity between the template and sensed complexes can then be assessed by comparing the multi-dimensional correlation value to a specified value such that if the value is exceeded, the two complexes are regarded as equivalent. One or more parameter feature sets may be incorporated into to the multiple-dimension correlation to further enhance its ability to classify depolarization complexes, where a parameter feature set is a set of deviations from a mean of measurable parameters related to the complex. Each parameter in the feature set may be treated as a sample of a new sensed waveform that is given a new orthogonal direction in the vector waveform.

DETAILED DESCRIPTION OF THE INVENTION

Certain cardiac rhythm management devices are capable of delivering various kinds of pacing therapy for preventing arrhythmias, and must therefore incorporate a means for recognizing those situations in which an arrhythmia is likely to occur. The present invention is directed toward a method and system for classifying cardiac depolarization complexes and is particularly suited for incorporation into such devices. Abnormal arrhythmogenic depolarization activity that propagates over the heart produces identifiable depolarization complexes that can be used as predictors of incipient arrhythmias. In order to classify a sensed depolarization complex as one which can lead to an arrhythmia, it must be determined if the complex is equivalent to a previously seen depolarization complex known to cause or predispose to the development of an arrhythmia. The known arrhythmogenic complex can thus be regarded as a template that can be compared with the sensed complex.

A depolarization complex is a temporally and spatially varying wave of depolarization spreading over the heart. A waveform associated with a depolarization complex can be sensed by an electrode. Such a waveform reflects the depolarization and repolarization activity taking place in the myocardium as the wave of depolarization spreads. A particular waveform of a sensed depolarization complex can be recorded from a single sensing channel and correlated with a template waveform belonging to a template depolarization complex. If the two waveforms are well correlated, it suggests that the template and sensed depolarization complexes that produced the waveforms are the same or very similar.

The statistical definition of the correlation R is the covariance of X and Y as normalized by the square root of the variance of X multiplied by the variance of Y:

$$R=\Sigma[(X-Xavg)(Y-Yavg)]/[\Sigma\{(X-Xavg)^2\}\Sigma\{(Y-Yavg)^2\}]^{1/2}$$

where X and Y are one-dimensional arrays of samples of the waveforms X(t) and Y(t), the summations are performed over the entire sample set contained in the arrays, and the mean values of X and Y are designated as Xavg and Yavg, respectively. The mean values Xavg and Yavg can either be calculated from the samples X and Y directly or from previous samples.

The above example of a one-dimensional correlation of sensed and template waveforms as recorded from a single channel thus provides a measure of the similarity between the sensed and template complexes. However, two substantially different depolarization complexes could nevertheless appear similar to a single sensing channel. This possibility would be greatly reduced if correlations could be performed on sensed waveforms recorded with two or more sensing channels having electrodes with different locations and orientations toward the heart.

Figure 1:
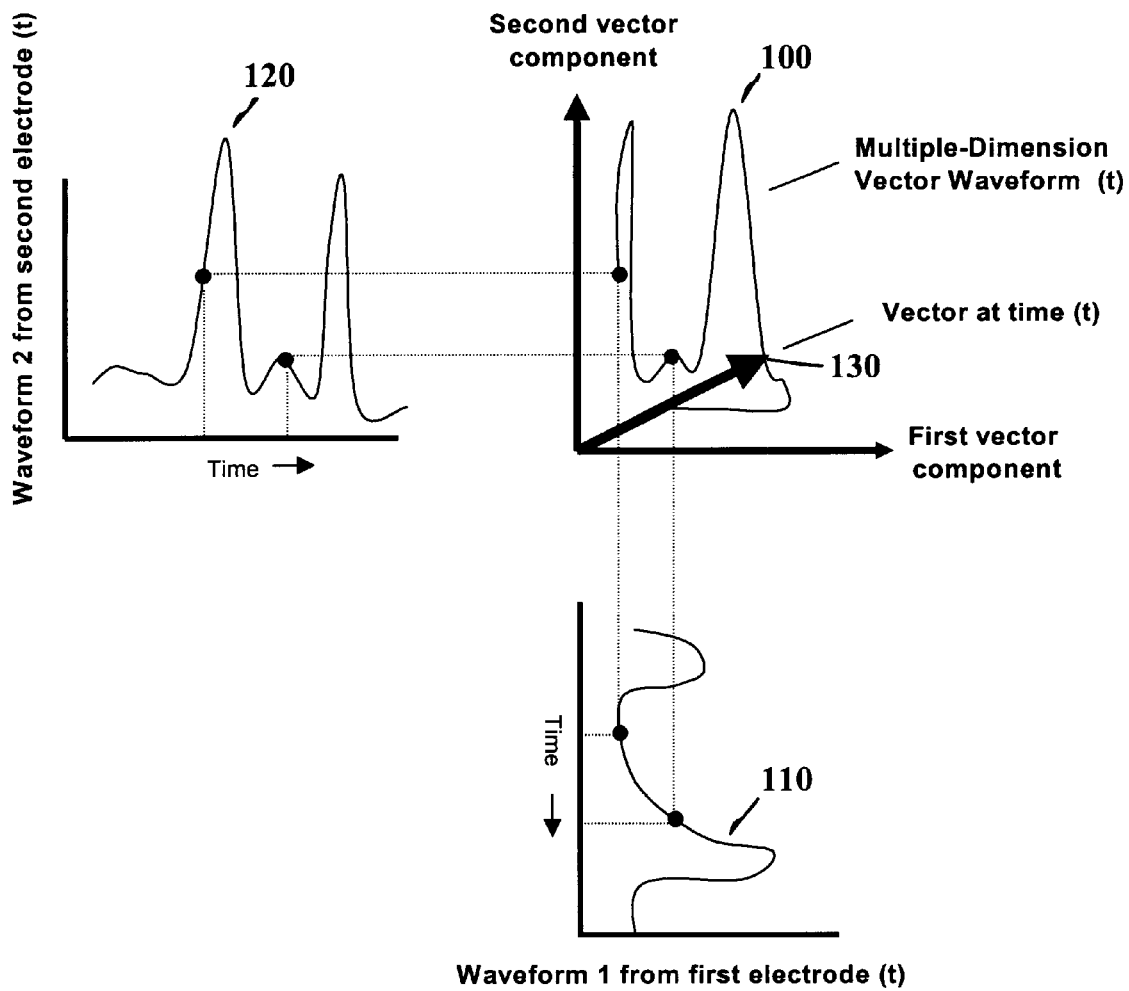
FIG. 1 is a diagram showing the waveforms sensed from two electrodes and resulting two-dimensional vector waveform.

A plurality of sensing channels may be used to record multiple sensed depolarization waveforms produced by a depolarization complex. The sensed depolarization waveforms can then be combined into a multi-dimensional vector with the sensed waveform from each of the electrodes being a different dimensional component of the mutliple-dimensional vector. FIG. 1 shows a two-dimensional vector waveform 100 whose x-axis component is comprised of the waveform 110 sensed by the first electrode and whose y-axis component is comprised of the waveform 120 sensed by the second electrode. The result is a vector waveform that moves about the x-y plane as a function of time. The heavy arrow 130 in FIG. 1 shows the two-dimensional vector waveform value at an instant in time. In the same way that a one-dimensional correlation is used to assess similarity of sensed and template complexes as seen by waveforms from a single electrode, multi-dimensional correlation as described below can be used to assess the similarity of sensed and template complexes as expressed by vector waveforms from the plurality of electrodes.

In accordance with the invention, a plurality of depolarization waveforms resulting from a cardiac depolarization complex are sensed with a plurality of separate electrodes and digital samples of the sensed waveforms are generated over a defined period of time to result in a sample set for each sensed waveform. The sample set of each sensed waveform is stored in a sensed sample array, and a mean waveform value is subtracted from each array member. The mean waveform value for each waveform may either be a specified value or computed as an average of the samples themselves. A similar sample set of each corresponding waveform of a template depolarization complex is stored in a template sample array with a mean waveform value subtracted from each array member. A correlation sum for the sensed depolarization complex and the template depolarization complex is then computed by multiplying each sensed sample array member by a corresponding template sample array member and summing the results of each such multiplication. An autocorrelation sum for the sensed complex is computed by multiplying each sensed sample array member by itself and summing the results of each such multiplication. An autocorrelation sum for the template complex is similarly computed by multiplying each template sample array member by itself and summing the results. A multi-dimensional correlation between the sensed and template depolarization complexes is then computed by dividing the correlation sum for the sensed and template complexes by the square root of the product of the autocorrelation sum for the sensed complex and the autocorrelation sum for the template complex. Similarity between the template and sensed complexes is then assessed by comparing the multi-dimension correlation value to a specified value, and if the value is exceeded, the sensed complex can be classified as equivalent to the template complex.

The method described above may be conceptualized in terms of vectors. The vector representing a depolarization complex sensed by the plurality of electrodes is expressed as $$\text{Vector waveform }(t)=\text{Waveform}_1(t)i+\text{Waveform}_2(t)j+\ldots+\text{Waveform}_n(t)z$$

where:

Waveform$_1$ (t) is the waveform sensed from the $1^{st}$ electrode, i is the unit vector in a first dimensional direction, Waveform$_2$ (t) is the waveform sensed from the $2^{nd}$ electrode, j is the unit vector in a second dimensional direction, . . .

Waveform$_n$ (t) is the waveform sensed from the $n^{th}$ electrode, and z is the unit vector in an $n^{th}$ dimensional direction.

The present invention treats these unit direction vectors as orthogonal but the sensed waveforms from the plurality of electrodes need not themselves be orthogonal.

The vector waveforms for sensed and template depolarization complexes can then be expressed as the n-dimensional vector functions of time:

$$\text{Template Vector }(t)=(T_1(t)-T_{1\,avg})i+(T_2(t)-T_{2\,avg})j+\ldots+(T_n(t)-T_{n\,avg})z$$

$$\text{Sensed Vector }(t)=(S_1(t)-S_{1\,avg})i+(S_2(t)-S_{2\,avg})j+\ldots+(S_n(t)-S_{n\,avg})z$$

where

Template Vector (t) is the n-dimensional vector waveform for the template complex Sensed vector (t) is the n-dimensional vector waveform for the sensed complex $T_1$ (t), $T_2$ (t), . . . , $T_n$ (t) are the waveforms from the first, second, . . . , and $n^{th}$ electrodes during the template depolarization complex.

$T_{1\,avg}$, $T_{2\,avg}$, . . . , $T_{n\,avg}$ are the average values for $T_1$, $T_2$, . . . $T_n$ $S_1(t), S_2(t), \ldots, S_n(t)$ are the waveforms from the first, second, ..., and $n_{th}$ electrodes during the sensed depolarization complex.

$S_{1\ avg}, S_{2\ avg}, \ldots, S_{n\ avg}$ are the average values for $S_1, S_2, \ldots, S_n$ The vector dot-product of these vector functions of time may then be written as:

$$TemplateVector(t) \cdot SensedVector(t) = [S_1(t) - S_{1avg}][T_1(t) - T_{1avg}] +$$

$$[S_2(t) - S_{2avg}][T_2(t) - T_{1avg}] +$$

$$\ldots + [S_n(t) - S_{navg}][T_n(t) - T_{navg}]$$

The correlation sum for the sensed and template vector waveforms is the sum across all samples in the sampled waveforms:

$$S\text{-}T\ Corrsum = \sum [TemplateVector(k) \cdot SensedVector(k)]$$

$$= \sum [(S_1(k) - S_{1avg})(T_1(k) - T_{1avg}) +$$

$$(S_2(k) - S_{2avg})(T_2(t) - T_{1avg}) + \ldots +$$

$$(S_n(k) - S_{navg})(T_n(t) - T_{navg})]$$

where the summation is taken over the entire sample set (i.e., from k=0 to k=N where N is the number of waveform samples), and S-T Corrsum is the correlation sum for the sensed and template vector waveforms. To normalize S-T Corrsum, the similar autocorrelation sums for the sensed vector with itself (S-S Corrsum) and the template vector with itself (T-T Corrsum) are also found. That is:

$$S\text{-}S\ Corrsum = \Sigma[(S_1(k)-S_{1\ avg})^2 + (S_2(k)-S_{2\ avg})^2 + \ldots + (S_n(k) - S_{n\ avg})^2]$$

and $$T\text{-}T\ Corrsum = \Sigma[(T_1(k)-T_{1\ avg})^2 + (T_2(k)-T_{2\ avg})^2 + \ldots + (T_n(k) - T_{n\ avg})^2]$$

where the summations are again taken over the entire sample set. The multidimensional correlation is then:

Multi-dimension Correlation=S-T Corrsum/[(S-S Corrsum) (T-T Corrsum)]$^{1/2}$

Other sensed parameters relating to a depolarization complex can also be incorporated into the multiple-dimensional correlation. A parameter feature set may be defined as a set of deviations from a set of mean values of measurable parameters related to a cardiac depolarization complex. Examples of such parameter features include signal amplitudes, QRS durations, QT intervals, ST segments, and time intervals associated with a depolarization complex. Such a parameter feature set may be incorporated into the multi-dimensional correlation by treating the feature set as a set of samples forming a new component direction for the sensed and template vector waveforms. For example, if the multiple-dimension correlation of the above example were to incorporate a five member feature set with values $SP_1$ to $SP_5$ during the sensed complex and values $TP_1$ to $TP_5$ during the template complex, then the resulting S-T correlation sum would become:

$$S\text{-}T\ Corrsum = \sum [(S_1(k) - S_{1avg})(T_1(k) - T_{1avg}) +$$

$$(S_2(k) - S_{2avg})(T_2(t) - T_{1avg}) + \ldots +$$

-continued $$(S_n(k) - S_{navg})(T_n(t) - T_{navg})] +$$

$$SP_1 TP_1 + SP_2 TP_2 + SP_3 TP_3 + SP_4 TP_4 + SP_5 TP_5$$

where the summation inside the brackets is taken over the sample set and additional contribution by the parameter feature set is added by summing over all features comprising the feature set.

Figure 2:
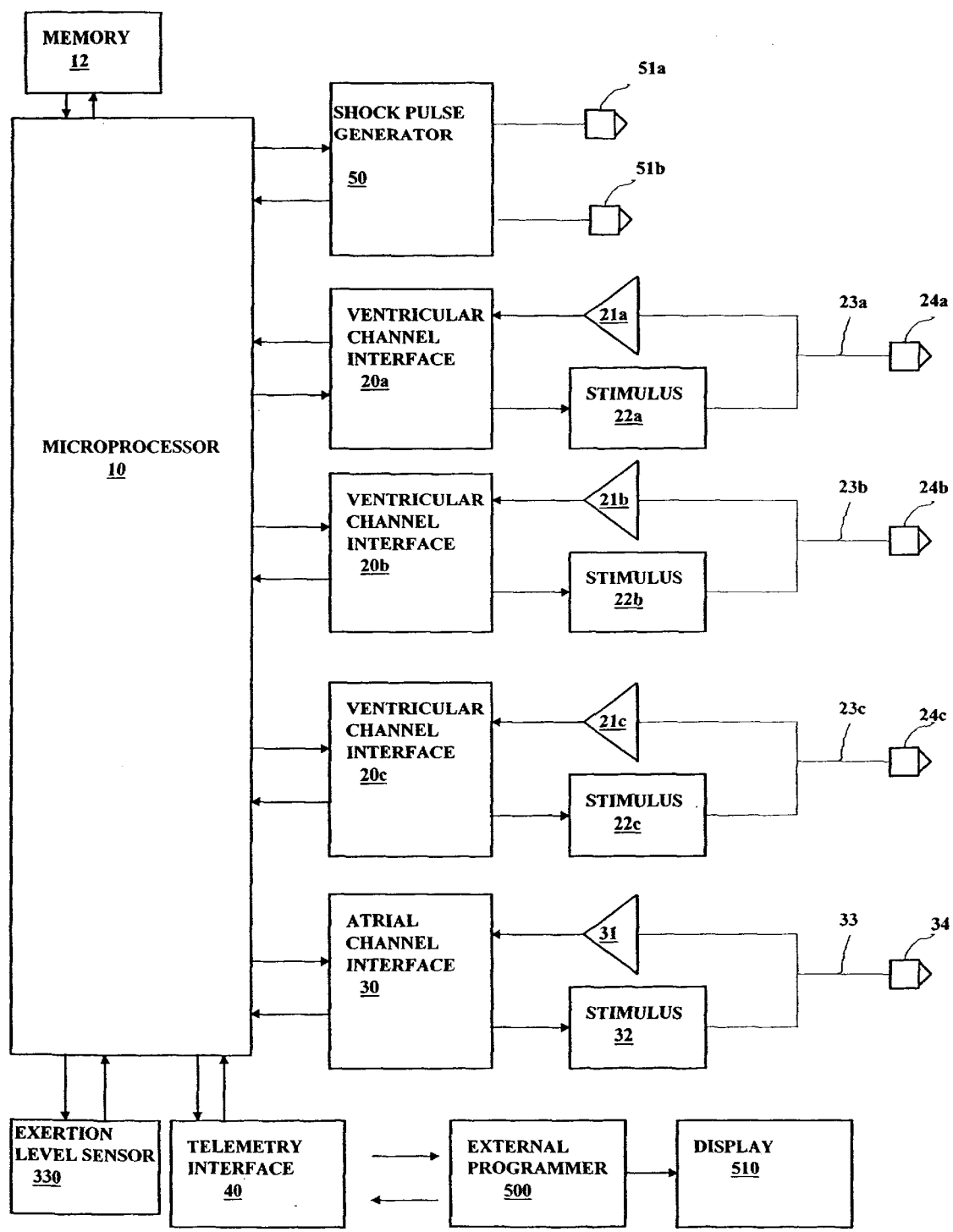
FIG. 2 is a diagram of a cardiac rhythm management device.

As aforesaid, a system in accordance with the invention may be incorporated into a cardiac rhythm management device. In the description of the particular embodiment that follows, a microprocessor-based cardiac rhythm management device incorporates such a system implemented as programmed instructions residing in memory that are executed by a microprocessor. FIG. 2 shows a system diagram of a microprocessor-based cardiac rhythm management device suitable for delivering various cardiac rhythm management therapies. The device is a pacemaker/ICD that is physically configured with sensing and pacing channels for both atria and both ventricles. The processor 10 of the device is a microprocessor that communicates with a memory 12 via a bidirectional data bus. The memory 12 typically comprises a ROM (read-only memory) for program storage and a RAM (random-access memory) for data storage. The pacemaker has an atrial sensing and pacing channel comprising electrode 34, lead 33, sensing amplifiers 31, pulse generators 32, and atrial channel interface 30 which communicates bidirectionally with microprocessor 10. The device also has a plurality of ventricular sensing and pacing/stimulation channels for one or both ventricles, three of which are shown as comprising electrodes 24a–c, leads 23a–c, sensing amplifiers 21a–c, pulse generators 22a–c, and ventricular channel interfaces 20a–c. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces 20a–c and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 that has an associated display 510. A shock pulse generator 50 is also interfaced to the microprocessor for delivering cardioversion or defibrillation pulses to the heart via a pair of terminals 51a and 51b that are connected by defibrillation leads to shock electrodes placed in proximity to regions of the heart.

The channel interfaces include signal conditioning circuitry and an analog-to-digital converter for producing digitized samples of the sensed waveforms. One function of the sensing channels is measuring heart rate in order to detect tachyarrythmias such as fibrillation. The ICD can detect a ventricular tachyarrhythmia, for example, by measuring a heart rate via the ventricular sensing channel and determining whether the rate exceeds a selected threshold value. Another function of the sensing channels is gathering digitized waveform samples in order to perform the correlation with a template waveform discussed above. The sensing channels may also detect parameter data such as signal amplitudes and time intervals from which parameter feature sets can be derived and incorporated into a vector waveform along with waveform samples.

Figure 3:
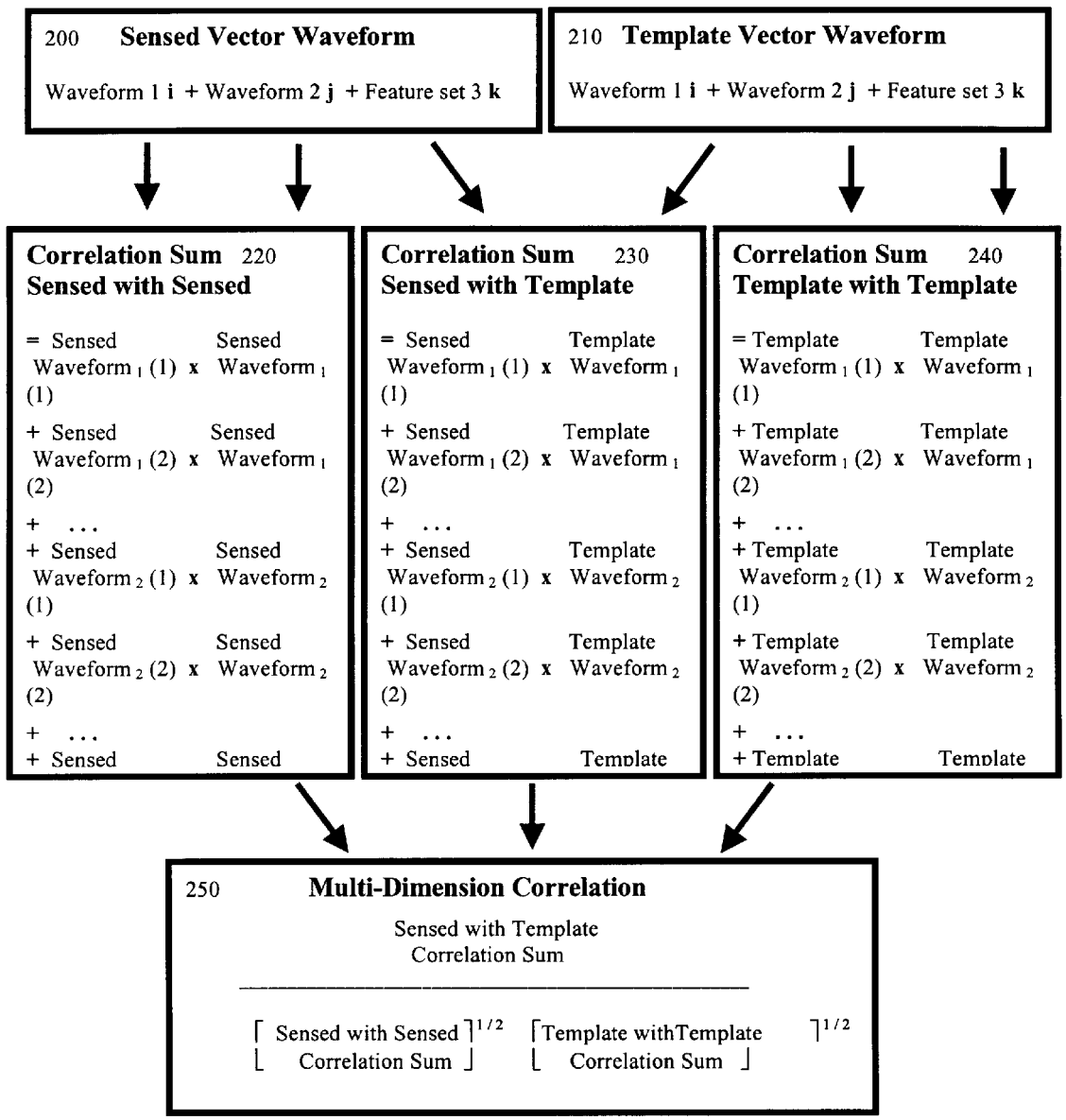
FIG. 3 is a block diagram of an exemplary implementation of multiple-dimensional correlation.

As stated, a system in accordance with the invention may be incorporated into the device of FIG. 2 as code executed by the microprocessor 10. Thus, waveforms are sensed and digitized by the sensing channels, and the digitized waveforms are then stored in memory as sample arrays. A representation of one or more template depolarization complexes is also stored in memory, each template complex comprising a plurality of template sample arrays and/or parameter features. FIG. 3 shows a block diagram of an exemplary implementation. A sensed vector waveform 200 comprises a sample array of a waveform 1, a sample array of a waveform 2, and a parameter feature array 3 containing one or more parameter features. A template vector waveform 210 comprises similar components corresponding to a template depolarization complex. The sensed-template correlator 230 performs the correlation sum operation for the sensed and template complexes. The sensed-sensed 220 and template-template 240 correlators perform the autocorrelation sums needed for normalization. The multi-dimensional correlation is then calculated by multi-dimensional correlator 250 from these correlation sums. The sensed cardiac depolarization complex is classified as being equivalent to the template complex if the multi-dimensional correlation value exceeds a specified value.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for classifying a sensed cardiac depolarization complex, comprising:

sensing a plurality of depolarization waveforms resulting from a cardiac depolarization complex with a plurality of separate electrodes and generating digital samples of the sensed waveforms over a defined period of time to result in a sample set for each sensed waveform;

storing the sample set of each sensed waveform in a sensed sample array and subtracting a mean waveform value from each array member;

storing a sample set of each corresponding waveform of a template depolarization complex in a template sample array and subtracting a mean waveform value from each array member;

computing a correlation sum for the sensed depolarization complex and the template depolarization complex by multiplying each sensed sample array member by a corresponding template sample array member and summing the results of each such multiplication;

computing an autocorrelation sum for the sensed complex by multiplying each sensed sample array member by itself and summing the results of each such multiplication;

computing an autocorrelation sum for the template complex by multiplying each template sample array member by itself and summing the results of each such multiplication;

computing a multi-dimensional correlation between the sensed and template depolarization complexes by dividing the correlation sum for the sensed and template complexes by the square root of the product of the autocorrelation sum for the sensed complex and the autocorrelation sum for the template complex; and, wherein the sensed depolarization complex is classified as being equivalent to the template complex if the multi-dimensional correlation exceeds a specified value.

2. The method of claim 1 wherein the mean values for the template and sensed waveforms are specified values for each such waveform.

3. The method of claim 2 further comprising averaging samples of a sensed waveform to compute a mean value for that waveform.

4. The method of claim 1 wherein samples of the sensed and template waveforms at a particular sampling time are grouped into a sensed complex vector and template complex vector, respectively, such that a correlation or autocorrelation sum constitutes a dot product of the vectors summed over the sample set.

5. The method of claim 4 further comprising adding one or more parameter features to the sensed and template complex vectors, wherein a parameter feature is defined as the deviation from a mean value of a measurable parameter related to a cardiac depolarization complex.

6. The method of claim 5 wherein a parameter feature added to the sensed complex vector and the template complex vector is a signal amplitude associated with a depolarization complex.

7. The method of claim 5 wherein a parameter feature added to the sensed complex vector and the template complex vector is a time interval associated with a depolarization complex.

8. The method of claim 7 wherein a parameter feature added to the sensed complex vector and the template complex vector is a QRS duration.

9. The method of claim 7 wherein a parameter feature added to the sensed complex vector and the template complex vector is a QT interval.

10. The method of claim 7 wherein a parameter feature added to the sensed complex vector and the template complex vector is an ST segment duration.

11. A cardiac rhythm management device having incorporated therein a system for classifying sensed cardiac depolarization complexes, comprising:

a plurality of sensing channels for sensing waveforms of a cardiac depolarization complex and for converting the sensed waveforms into digitized samples;

a processor and associated memory interfaced to the sensing channels; and, wherein the processor is programmed to:

store digital samples of the sensed waveforms for each sensed waveform over a defined period of time to result in a sample set;

store the sample set of each sensed waveform in a sensed sample array and subtracting a mean waveform value from each array member;

store a sample set of each corresponding waveform of a template depolarization complex in a template sample array and subtracting a mean waveform value from each array member;

compute a correlation sum for the sensed depolarization complex and the template depolarization complex by multiplying each sensed sample array member by a corresponding template sample array member and summing the results of each such multiplication;

compute an autocorrelation sum for the sensed complex by multiplying each sensed sample array member by itself and summing the results of each such multiplication;

compute an autocorrelation sum for the template complex by multiplying each template sample array member by itself and summing the results of each such multiplication;

compute a multi-dimensional correlation between the sensed and template depolarization complexes by dividing the correlation sum for the sensed and template complexes by the square root of the product of the autocorrelation sum for the sensed complex and the autocorrelation sum for the template complex; and, classify the sensed depolarization complex as being equivalent to the template complex if the multi-dimensional correlation exceeds a specified value.

12. The device of claim 11 wherein the mean values for the template and sensed waveforms are specified values for each such waveform.

13. The device of claim 12 wherein the processor is programmed to average samples of the sensed waveforms to compute a mean value.

14. The device of claim 11 wherein the processor is programmed to group samples of the sensed and template waveforms at a particular sampling time into a sensed complex vector and template complex vector, respectively, such that a correlation or autocorrelation sum constitutes a dot product of the vectors summed over the sample set.

15. The device of claim 14 wherein the processor is programmed to add one or more parameter features to the sensed and template complex vectors, wherein a parameter feature is defined as the deviation from a mean value of a measurable parameter related to a cardiac depolarization complex.

16. The device of claim 15 wherein a parameter feature added to the sensed complex vector and the template complex vector is a signal amplitude associated with a depolarization complex.

17. The device of claim 15 wherein a parameter feature added to the sensed complex vector and the template complex vector is a time interval associated with a depolarization complex.

18. The device of claim 17 wherein a parameter feature added to the sensed complex vector and the template complex vector is a QRS duration.

19. The device of claim 17 wherein a parameter feature added to the sensed complex vector and the template complex vector is a QT interval.

20. The device of claim 17 wherein a parameter feature added to the sensed complex vector and the template complex vector is an ST segment duration.

* * * * *